United States Patent
Behar-Cohen et al.

(10) Patent No.: US 9,315,829 B2
(45) Date of Patent: Apr. 19, 2016

(54) METHODS FOR INTRACELLULAR DELIVERY OF NUCLEIC ACIDS

(75) Inventors: Francine Behar-Cohen, Paris (FR); Elodie Touchard, La Milesse (FR)

(73) Assignee: UNIVERSITE PARIS DESCARTES, Paris (FR)

( * ) Notice: Subject to any disclaimer, the term of this patent is extended or adjusted under 35 U.S.C. 154(b) by 0 days.

(21) Appl. No.: 13/522,839

(22) PCT Filed: Jan. 14, 2011

(86) PCT No.: PCT/IB2011/050174
§ 371 (c)(1),
(2), (4) Date: Sep. 18, 2012

(87) PCT Pub. No.: WO2011/089541
PCT Pub. Date: Jul. 28, 2011

(65) Prior Publication Data
US 2013/0012573 A1   Jan. 10, 2013

(30) Foreign Application Priority Data

Jan. 19, 2010 (EP) ..................................... 10305060

(51) Int. Cl.
*A61K 48/00* (2006.01)
*A61P 27/02* (2006.01)
*A61P 29/00* (2006.01)
*C07J 1/00* (2006.01)
*C12N 15/87* (2006.01)
*C07K 14/72* (2006.01)

(52) U.S. Cl.
CPC ............ *C12N 15/87* (2013.01); *A61K 48/0083* (2013.01); *C07K 14/721* (2013.01); *C12N 2501/39* (2013.01); *C12N 2510/00* (2013.01)

(58) Field of Classification Search
CPC ................................................ A61K 48/0016
See application file for complete search history.

(56) References Cited

U.S. PATENT DOCUMENTS

| 4,466,442 | A | 8/1984 | Hilmann et al. |
| 4,684,479 | A | 8/1987 | D'Arrigo |
| 4,718,433 | A | 1/1988 | Feinstein |
| 5,088,499 | A | 2/1992 | Unger |
| 5,123,414 | A | 6/1992 | Unger |
| 5,271,928 | A | 12/1993 | Schneider et al. |
| 5,413,774 | A | 5/1995 | Schneider et al. |
| 5,445,813 | A | 8/1995 | Schneider et al. |
| 5,556,610 | A | 9/1996 | Yan et al. |
| 5,597,549 | A | 1/1997 | Schneider et al. |
| 5,686,060 | A | 11/1997 | Schneider et al. |
| 5,773,527 | A | 6/1998 | Tomalia et al. |
| 5,798,091 | A | 8/1998 | Trevino et al. |
| 5,827,504 | A | 10/1998 | Yan et al. |
| 6,217,850 | B1 | 4/2001 | Dugstad et al. |
| 6,245,318 | B1 | 6/2001 | Klibanov et al. |
| 6,264,917 | B1 | 7/2001 | Klaveness et al. |
| 6,416,740 | B1 | 7/2002 | Unger |
| 6,443,898 | B1 | 9/2002 | Unger et al. |
| 6,656,916 | B1 | 12/2003 | Schwarz et al. |
| 2002/0065213 | A1* | 5/2002 | Debs .................................. 514/2 |
| 2002/0159952 | A1 | 10/2002 | Unger |
| 2005/0244378 | A1 | 11/2005 | Kaufman et al. |
| 2005/0260189 | A1 | 11/2005 | Klibanov et al. |
| 2008/0063604 | A1 | 3/2008 | Claudio |

FOREIGN PATENT DOCUMENTS

| EP | 0 458 745 A1 | 11/1991 | |
| WO | WO 92/15680 A1 | 9/1992 | |
| WO | WO 2006/111490 A1 | 10/2006 | |
| WO | WO 2006/123248 A2 | 11/2006 | |
| WO | WO 2008/069942 A2 * | 6/2008 | ............. C12N 15/86 |
| WO | 2009/129464 A2 | 10/2009 | |

OTHER PUBLICATIONS

Malone et al., Dexamethasone Enhancement of Gene Expression after Direct Hepatic DNA Injection. JBC, 1994, 269(47):29903-7.*
Shen et al., Dynamics of phosphorothioate oligonucleotides in normal and laser photocoagulated retina. Br J Ophthalmol 1999;83:852-861.*
Bloquel et al.; "Plasmid electrotransfer of eye ciliary muscle: principles and therapeutic efficacy using hTNF-α soluble receptor in uveitis;" The FASEB Journal; 2006; pp. 389-391.
Touchard et al.; "Effects of ciliary muscle plasmid electrotransfer of TNF-α soluble receptor variants in experimental uveitis;" Gene Therapy; 2009; vol. 16.; pp. 862-873.
Dayton et al.; "Targeted Imaging Using Ultrasound;" Journal of Magnetic Resonance Imaging; 2002; vol. 16; pp. 362-377.
Bloch et al.; "Targeted Imaging Using Ultrasound Contrast Agents;" IEEE Engineering in Medicine and Biology Magazine; Sep./Oct. 2004; pp. 18-29.
Sonoda et al., "Gene Transfer to Corneal Epithelium and Keratocytes Mediated by Ultrasound with Microbubbles;" Investigative Ophthalmology & Visual Science; Feb. 2006; vol. 47; No. 2; pp. 558-564.
Aug. 25, 2011 International Search Report issued in International Application No. PCT/EP2011/063631.
Aug. 25, 2011 Written Opinion issued in International Application No. PCT/EP2011/063631.
U.S. Appl. No. 13/816,368, filed Feb. 11, 2013, in the name of Francine Behar-Cohen et al.
Park et al.; "Periocular Triamcinolone Enhances Intraocular Gene Expression after Delivery by Adenovirus;" Investigative Ophthalmology & Visual Science; Jan. 2008; vol. 49; No. 1; pp. 399-406.
Bernasconi et al.; "Cortisol increases transfection efficiency of cells;" FEBS Letters; Dec. 8, 1997; vol. 419, No. 1, pp. 103-106.

(Continued)

*Primary Examiner* — Scott Long
*Assistant Examiner* — Arthur S Leonard
(74) *Attorney, Agent, or Firm* — Oliff PLC

(57) ABSTRACT

A method for intracellular delivery of isolated naked nucleic acids into a biological tissue or organ, that includes (a) contacting the tissue or organ with an efficient amount of at least one active corticosteroid, and (b) contacting the tissue or organ treated in step b with an efficient amount of isolated naked nucleic acids, wherein step (a) is carried out for a period of time ranging from at least five minutes to at most two hours and being immediately followed by step (b).

6 Claims, 8 Drawing Sheets

(56) References Cited

OTHER PUBLICATIONS

Figure 1:
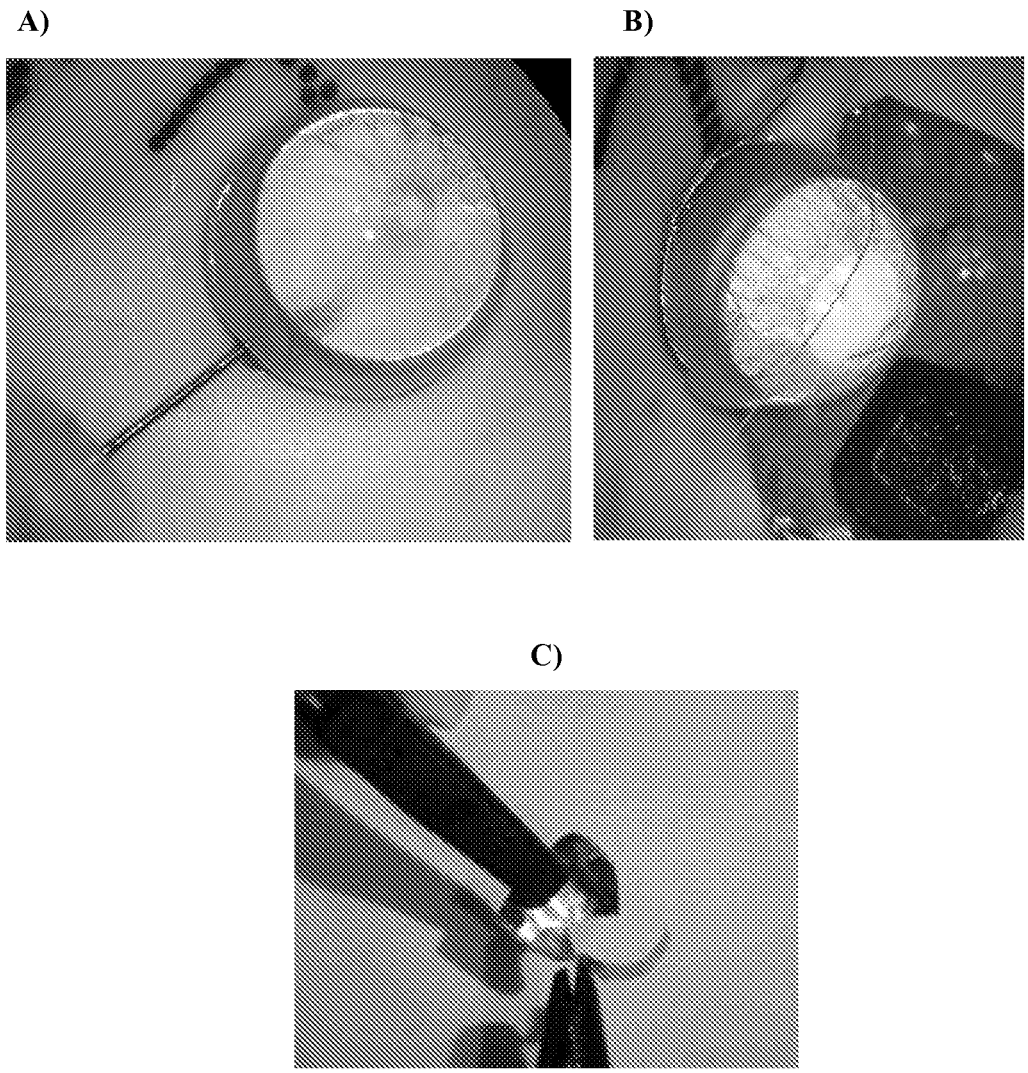

Braun et al.; "In vitro and in vivo effects of glucocorticoids on gene transfer to skeletal muscle;" FEBS Letters; Jul. 9, 1999; vol. 454; No. 3; pp. 277-282.

Wiseman et al.; "Steroid hormone enhancement of gene delivery to a human airway epithelial cell line in vitro and mouse airways in vivo;" Gene Therapy; Oct. 2001; vol. 8; No. 20; pp. 1562-1571.

Ma Kun et al.; "Structure-transfection activity relationships with glucocorticoid-polyethyl-enimine conjugate nuclear gene delivery systems;" Biomaterials; Aug. 2009; vol. 30; No. 22; pp. 3780-3789.

De Perrot et al.; "Impact of Human Interleukin-10 on Vector-Induced Inflammation and Early Graft Function in Rat Lung Transplantation;" American Journal of Respiratory Cell and Molecular Biology, American Lung Association, May 1, 2003; vol. 28; No. 5; pp. 616-625.

Kowalczuk et al.; "Local Ocular Immunomodulation Resulting from Electrotransfer of Plasmid Encoding Soluble TNF Receptors in the Ciliary Muscle;" Investigative Opthalmology and Visual Science Association for Research in Vision and Ophthalmology; Apr. 2009; vol. 50, No. 4, pp. 1761-1768.

Bloquel et al.; "Non-viral ocular gene therapy: Potential ocular therapeutic avenues;" Advanced Drug Delivery Reviews; Nov. 15, 2006; vol. 58, No. 11, pp. 1224-1242.

Apr. 12, 2011 International Search Report issued in International Application No. PCT/IB2011/050174.

Apr. 12, 2011 Written Opinion issued in International Application No. PCT/IB2011/050174.

Jun. 28, 2010 European Search Report issued in Application No. EP 10 30 5060.

Martin et al., "Gene Therapy for Optic Nerve Disease," Eye, vol. 18, pp. 1049-1055, 2004.

Martin et al., "Gene Therapy with Brain-Derived Neurotrophic Factor As a Protection: Retinal Ganglion Cells in a Rat Glaucoma Model," Investigative Ophthalmology & Visual Science, vol. 44, No. 10, pp. 4357-4365, Oct. 2003.

Hauswirth et al., "Ocular Gene Therapy: Quo Vadis?," Investigative Ophthalmology & Visual Science, vol. 41, No. 10, pp. 2821-2826, Sep. 2000.

Bloquel et al., "Plasmid Electrotransfer of Eye Ciliary Muscle: Principles and Therapeutic Efficacy using hTNF-$\alpha$ Soluble Receptor in Uveitis," The FASEB Journal, Express Article 10.1096/fj.05-4737fje., pp. 1-22, Published online Dec. 13, 2006.

Zhang et al., "Multifunctional Microbubbles for Image-Guided Antivascular Endothelial Growth Factor Thereapy," Journal of Biomedical Optics, vol. 15, No. 3, pp. 030515-1-030515-3.

Nov. 7, 2013 Office Action issued in U.S. Appl. No. 13/816,368.
Jul. 8, 2014 Office Action issued in U.S. Appl. No. 13/816,368.
Jun. 19, 2015 Office Action issued in U.S. Appl. No. 13/816,368.

\* cited by examiner

METHODS FOR INTRACELLULAR DELIVERY OF NUCLEIC ACIDS

The instant invention relates to intracellular delivery methods, and more particularly to methods for improving the intracellular delivery of a nucleic acid into an animal cell. The invention also relates to uses, kits and compositions useful for implementing the novel methods of the invention. More particularly the present invention is directed to a method for improving intracellular delivery of nucleic acids into the ocular sphere of an individual in need thereof. The present invention also relates to novel methods, uses, kits and compositions useful for gene therapy, in particular for gene therapy of the eyes.

Gene therapy requires the ability to efficiently transfer nucleic acids into a cell.

Intracellular delivery, or transfection, of nucleic acids into cells typically requires that the cells be competent, i.e. that they have transient pores or "holes" in their cell membrane, to allow the uptake of the material. Some cells are naturally competent, as bacteria, but numerous other cells, as animal cells, are poorly or even non-competent.

A naturally competent cell may uptake naked isolated nucleic acid, whereas poorly or non-competent cell needs to be rendered competent. For example, cells from ophthalmic tissue, such as cells from retina, RPE/choroid complex, or neuroepithelia are known to be non-competent cells and to be very difficult to transfect with naked nucleic acids.

So far numerous techniques have been proposed to deliver or transfect nucleic acids into non-competent cells. Those techniques may be sorted as chemical, biological, mechanical or physical techniques.

As examples of chemical techniques well-known in the art, one may mention the use of calcium phosphate, the use of a cationic lipid to produce liposomes, the use of virosomes, or the use of polymers, such as poloxamines, polyethyleneimine or DEAE-dextran.

As examples of biological techniques, one may mention the use of adenovirus.

As examples of physical or mechanical techniques, one may mention thermal treatment (chill exposure), sonoporation, that is the use of ultrasounds, electroporation, that is the application of an electrical field to the cells or the tissue to be transfected, magnet assisted transfection using magnetic nanoparticles, optical transfection using a highly focused laser to transiently create a hole in the cell membrane or the gene-gun technique using nanoparticle of an inert solid, commonly gold.

It may also be possible to combine some of those techniques, such as the use of a polymer and electroporation.

Although very useful, those techniques are crippled with numerous inconvenients such as the requirement of delicate adjustments according to the kind of nucleic acid to be delivered or to the cells to be transfected. Besides, some techniques, in particular chemical or biological techniques may inherently be associated with toxic effect or may transform the cells to be transfected, modifying drastically their phenotype. Consequently, most of those techniques are not accepted in gene therapy in human or animal.

Besides, although some of the above-described techniques have proven useful for the cell transfection of ophthalmic tissue from small or new-born animals (small eyeball), they have proven far less efficient in adult ophthalmic tissue or in eyeballs the size of human eyeballs.

Furthermore, in the particular area of the eye, a major problem in gene therapy of eye diseases and disorders is the difficulty in delivering nucleic acids into the eye at therapeutically or prophylactically effective concentrations. In particular it may be problematic to introduce nucleic acids into the eye without induction of an inflammatory response.

Therefore, there is a lack of means of transducing terminally differentiated or non-proliferating cells, in particular human cells, within the eye.

Recently, the inventors have proposed in WO 2006/123248 a novel electroporation technique to deliver nucleic acids material into cells of ophthalmic tissue. Although very useful, this technique may be difficult to implement and may require extensive skills and training to be carried out, in particular for in vivo situations.

Thus, despite the above-described attempts to provide effective methods, there remains a long-felt and acute need for new approaches to deliver naked nucleic acids into cells and to treat ocular diseases, in particular intra-ocular diseases.

There is also a need for a novel method for intracellular delivering of naked nucleic acids that may be easy, simple, and handy to use.

There is a need for a novel method that may efficiently increase the intracellular delivery of naked nucleic acids into non-competent cells, in particular from ophthalmic tissue.

There is also a need for a novel method that may efficiently increase the intracellular delivery of naked nucleic acid into cells of ophthalmic tissue, in vitro, ex vivo or in vivo.

There is also a need for a novel method that may efficiently increase the intracellular delivery of naked nucleic acid into cells of adult ophthalmic tissue, and in particular in the adult retina.

There is a need for a novel method that is non toxic or has a reduced or acceptable toxicity for use in vitro, ex vivo or in vivo, and in particular that does not result in inflammatory processes.

There is a need for a novel method that is cost-effective to implement.

The instant invention has for purpose to satisfy those needs.

The present inventors have now developed a novel method for delivering a naked nucleic acid, in particular into the ocular area.

Therefore, according to one embodiment the invention relates to a method for intracellular delivery of at least one isolated naked nucleic acid into an animal cell, said method comprising at least the steps of:

a/ contacting said animal cell with an efficient amount of at least one active corticosteroid, and b/ contacting said animal cell treated in step a/ with an efficient amount of at least one isolated naked nucleic acid, said step a/ being carried out for a period of time ranging from at least five minutes to at most two hours and being immediately followed by step b/.

Preferably, the animal cell may be an isolated animal cell, in particular provided in the form of an isolated biological tissue or organ.

According to another embodiment, the invention relates to a method for intracellular delivery of at least one isolated naked nucleic acid into a biological tissue or organ, said method comprising at least the steps of:

a/ contacting said biological tissue or organ with an efficient amount of at least one active corticosteroid, and b/ contacting said biological tissue or organ treated in step a/ with an efficient amount of at least one isolated naked nucleic acid;

said step a/ being carried out for a period of time ranging from at least five minutes to at most two hours and being immediately followed by step b/.

Within the invention, the expression "for a period of time" intends to mean the amount of time during which a cell, a tissue or an organ is contacted with or are in presence of a corticosteroid. In case of in vivo application, it means that, considering the individual to be treated and the pharmacodynamic properties of the corticosteroid, the latter is administrated by means and in amount suitable for the target cells of the individual to be in contact with the corticosteroid during the indicated period of time.

Surprisingly, the inventors have observed, as exposed in the example section, that the treatment of cells or a tissue, in particular non-competent cells or tissue, such as an ophthalmic tissue, and more particularly retina, RPE/choroid complex or ciliary muscle, with a corticoid, in particular triamcinolone, such as triamcinolone acetate, or anecortave, such as anecortave acetonide, for 5 min to two hours before application of a naked isolated nucleic acid resulted in a dramatic improvement of intracellular delivery of the nucleic acid into the non-competent cells or tissue, without the need to resort to the use of a chemical, biological, mechanical or physical method for transfection.

The inventors have also observed that the exposure of poorly competent cells, such as striated muscle cells to a corticoid, in particular dexamethasone, for 5 min to two hours before application of a naked isolated nucleic acid resulted in a dramatic improvement of intracellular delivery of the nucleic acid into those cells without the need to resort to the use of a chemical, biological, mechanical or physical method for transfection.

The use of corticosteroids or glucocorticoids in various methods for intracellular gene delivery has been described. They are used either after the step of gene delivery, for increasing the gene expression as in U.S. Pat. No. 6,656,916, or a few days before the step of gene delivery to reduce the inflammatory reaction associated with adenovirus delivery of gene, as in Park et al. (Invest. Ophtalmol. Vis. Sci. 2008, 49:399). Steroids were also proposed to be used prior the administration of adenoviruses for reducing inflammations associated with this administration, and enhancing the activity of the CMV promoter to increase gene expression (WO 2008/069942). Glucocorticoids have also been proposed for enhancing the gene uptake or expression of DNA transfected with polyethylene imine, calcium phosphate, adenovirus or liposome (Bernasconi et al., FEBS Lett., 1997, 419:103; Braun et al., FEBS Lett., 1999, 454:277; Wiseman et al., Gene Therapy, 2001, 8:1562).

However, up to now, corticosteroids, and in particular glucocorticoids, have never been proposed to enhance as such delivery of isolated naked nucleic acids into non-competent or poorly competent cells.

Within the invention, the expression "isolated naked nucleic acid" is intended to mean a nucleic acid molecule which is not associated with or which is not mixed with or which is free of any synthetic, biosynthetic, chemical, biological or mechanical agent used for the intracellular delivery of nucleic acids such as cationic polymers, liposomes, adenovirus or golden particles. Accordingly, a naked nucleic acid is a nucleic acid which is free of any interaction with any moiety which could be used to favour its entrance into an animal cell.

Within the invention, the term "animal" is intended to mean any multicellular, eukaryotic organism of the kingdom Animalia or Metazoa, including human.

Within the invention, the expression "efficient amount" is intended to mean the at least minimal amount of a given substance necessary to achieve a given effect associated to this substance.

According to one embodiment, a method of the invention does not comprise the use of any chemical, biological, mechanical or physical techniques used for intracellular delivery of nucleic acids, being understood that the use of a corticosteroid in accordance with the invention does not enter in any of those categories.

According to another embodiment, a method of the invention does not comprise reducing an inflammatory process or activating gene expression through pharmacological response induced by the corticosteroid.

According to another embodiment, a method of the invention does not comprise enhancing the activity of a CMV promoter.

According to another embodiment, the instant invention also relates to a kit for intracellular delivery of at least one isolated naked nucleic acid in an animal cell, in particular for gene therapy, comprising:
  a/ at least one corticosteroid,
  b/ at least one isolated naked nucleic acid, and
  c/ at least one instruction comprising a first step of treating said animal cell with said corticosteroid for at least 5 minutes to at most 2 hours, and a second step of contacting said treated animal cell with said isolated naked nucleic acid, said second step being carried out immediately after said first step.

According to another embodiment, the instant invention also relates to a use of at least one corticosteroid for the preparation of a pharmaceutical composition, as active agent for promoting intracellular delivery of an isolated naked nucleic acid in an individual in need thereof, in particular for gene therapy, said pharmaceutical composition being intended to be administered to said individual at least 5 min to at most 2 hours before administering to said individual said isolated naked nucleic acid.

According to another embodiment, the instant invention also relates to a corticosteroid in a pharmaceutical composition, as active agent for promoting intracellular delivery of an isolated naked nucleic acid in an individual in need thereof, in particular for gene therapy, said pharmaceutical composition being intended to be administered to said individual at least 5 min to at most 2 hours before administering to said individual said isolated naked nucleic acid.

According to one of its advantages, the instant invention provides a novel, efficient, and easy to use method for improving the intracellular delivery of isolated naked nucleic acids into non-competent or poorly competent cells.

Within the invention, the expressions "non-competent" or "poorly competent" in regard to biological tissues or organ or animal cells intend to mean that those tissues or cells cannot be transfected or cannot be transfected with a sufficient yield with nucleic acids without resorting to a chemical, biological, mechanical or physical method for transfection usually implemented for transfecting nucleic acids in vitro, ex vivo, or in vivo. In particular a "non-competent" or "poorly competent" cell may be post-mitotic or quiescent cell.

According to another of its advantages, the instant invention also provides a cost-effective method for improving the intracellular delivery of isolated naked nucleic acids into non-competent or poorly competent cells.

According to another of its advantages, a method of the invention may resort to well-known and accepted corticosteroids, in particular glucocorticoids, in veterinary or medical practice.

According to another of its advantages, a method of the invention may be no or weakly toxic, or may be associated with no or well-accepted side-effects in veterinary or medical practice compared to methods requiring the use of chemical, biological, mechanical or physical auxiliary treatments for intracellular delivery of nucleic acids.

Methods

A method according to the invention comprises at least a first step a/ of contacting at least one animal cell, in particular one isolated animal cell, or one biological tissue, in particular one isolated biological tissue, with an efficient amount of at least one corticosteroid.

In a preferred embodiment, an animal cell to be transfected may be provided in the form of a biological tissue or an organ.

According to an embodiment, the period of time of step a/ may range from 10 to 90 min, in particular from 10 to 60 min, in particular from 15 to 45 min, and more particularly from 15 to 30 min.

Immediately, further to step a/, a second step b/ of contacting said animal cell or biological tissue with an efficient amount of at least one isolated naked nucleic acid is carried out.

Within the invention the term "immediately" in regard to steps a/ and b/ is intended to mean that step b/ is performed upon completion of step a/, without any intermediary steps. One having skills in the art naturally understands that between step a/ and step b/, the animal cell or biological tissue may be subjected to a time elapsing and/or a certain amount of manipulations required for implementing step b/, and which are not to be construed as additional intermediary steps.

In step a/ or b/, the step of contacting may be performed according to any suitable method known in the art.

For example, when the cells or tissues to be transfected are on a culture plate, the step of contacting may be carried out by applying a first solution containing the corticosteroid to said cells or tissues, then, with or without washing the first solution, applying a second solution containing the nucleic acid.

When the cells or tissues to be transfected are parts of a body of an animal, for example a human, and in particular an eye of a human, the step of contacting may be carried out by contacting, for example by injecting, a first solution containing the corticosteroid into the part of the body of said animal comprising said cells or tissues, then contacting, for example by injecting, a second solution containing the nucleic acid.

According to one embodiment, when the animal cell or biological tissue to be treated are in the eye, the corticosteroid and the nucleic acid may be administered by transconjunctival, transscleral, transcorneal, intraocular (preferably during surgery) or endoscopic route.

Administration may be performed during vitrectomy.

Administration may be performed by injection, in particular by a unique injection site or at multiple injection sites.

An injection may be performed using any known methods and devices in the art. In particular, an injection may be carried out in an eye with a microfine syringe, and in particular a 30 G needle 100 µl microfine syringe.

According to another embodiment, the steps of contacting with ophthalmic tissue may also be performed by spraying or instilling corticosteroids and nucleic acids onto the surface of an eye.

According to another embodiment, the steps of contacting may be performed by oral administration, mucosal administration, such as nasal or rectal administration, or topical administration by application of the corticosteroid and nucleic acids onto the skin.

Another aspect of the invention relates to a method, in particular a method for gene therapy, for replacing (or acting in place of) or for correcting a functionally deficient endogenous gene, for conferring to the host the ability to produce a therapeutic polypeptide, for causing repression of an undesirable gene product, or to stimulate an immune response.

In another embodiment, the invention relates to a delivery of a nucleic acid into a cell, in particular an ocular cell, in order to obtain a cell, a tissue, an organ or an animal which may serve as a model for studying for example a disease, in particular an ocular disease or for screening compounds capable of treating said disease.

Individuals who may beneficiate of the above-described methods, therapeutic or prophylactic, may be any animal, in particular any mammalian, preferably a human that suffers or may suffer from any diseases, such an eye disease or eye condition, which may benefit from a treatment with a nucleic acid.

The invention thus relates to the use of a method of the invention to prevent or treat various diseases, in particular ocular diseases or impairments of the eyes, including but not limited to ocular inflammatory diseases, ischemic diseases, proliferative diseases (for example a neovascular or a glial disease), neurodegenerative diseases and glaucoma, either alone or in combination with additional treatments.

A further object of the invention is a method of producing a protein, in particular therapeutic or prophylactic protein in individual ocular tissue(s) or cells comprising administering a nucleic acid encoding said protein to said ocular tissue(s) or cells, wherein said nucleic acid is delivered to said ocular tissue(s) or cells according to a method comprising at least the steps of:

a/ contacting said ocular tissue(s) or cells with an efficient amount of at least one active corticosteroid, and b/ contacting said ocular tissue(s) or cells treated in step a/ with an efficient amount of at least one isolated naked nucleic acid encoding said protein, said step a/ being carried out for a period of time ranging from at least five minutes to at most two hours and being immediately followed by step b/ and said protein being expressed.

According to one embodiment, said ocular tissue(s) or cells are isolated tissue(s) or cells.

The invention also relates to a method of protecting an individual against an ocular disease or impairment of an eye comprising administering a nucleic acid into said eye of said individual in need thereof, wherein said nucleic acid is delivered to ocular tissue(s) or cells of said eye according to a method comprising at least the steps of:

a/ contacting said ocular tissue(s) or cells with an efficient amount of at least one active corticosteroid, and b/ contacting said ocular tissue(s) or cells treated in step a/ with an efficient amount of at least one isolated naked nucleic acid, said step a/ being carried out for a period of time ranging from at least five minutes to at most two hours and being immediately followed by step b/, and protecting said eye against the ocular disease.

Still another aspect of the invention is a method of treating an ocular disease or an impairment of an eye affecting an individual comprising administering to said eye of said individual in need thereof a nucleic acid, wherein said nucleic acid is delivered to ocular tissue(s) or cells of said eye according a method comprising at least the steps of:

a/ contacting said ocular tissue(s) or cells with an efficient amount of at least one active corticosteroid, and b/ contacting said ocular tissue(s) or cells treated in step a/ with an efficient amount of at least one isolated naked nucleic acid, said step a/ being carried out for a period of time ranging from at least five minutes to at most two hours and being immediately followed by step b/.

Biological Tissues & Animal Cells

According to a particular embodiment, an animal cell or biological tissue suitable for the invention may be a non-competent cell or tissue or a poorly competent cell or tissue.

In particular, an animal cell or biological tissue considered in the invention may be a non-competent cell or tissue.

According to an embodiment, a biological tissue or organ to be transfected preferably comprises non-competent cells.

As examples of non-competent or poorly competent cells or tissues, one may mention ophthalmic tissue, retina cells, RPE/choroid complex cells, ciliary muscle cells, corneal cells, or neuronal cells, in particular from an adult animal.

According to a preferred embodiment, an animal cell suitable for the invention may be chosen in the group consisting of a smooth muscle cell, in particular a ciliary muscle cell, a striated muscle cell, a retina cell, a RPE/choroid complex cell, a neuronal cell, a cutaneous epithelia cell, a dermal cell, a vascular endothelial cell, a corneal endothelial cell, a corneal epithelial cell, a glial retinal cell, a photoreceptor cell, a keratocyte, and an epithelial lung cell.

According to another preferred embodiment, a biological tissue or organ suitable for the invention may be chosen in the group consisting of a smooth muscle tissue, in particular a ciliary muscle, a striated muscle, a retina tissue, a RPE/choroid complex tissue, a brain tissue, a cutaneous epithelium, a dermal tissue, a vascular endothelium, a corneal endothelium, a corneal epithelium, a glial retinal tissue, a photoreceptor cell, a tissue comprising keratocytes, and an epithelial lung tissue.

According to a preferred embodiment, an animal cell suitable for the invention may be chosen in the group consisting of a smooth muscle cell, in particular a ciliary muscle cell, a retina cell, a RPE/choroid complex cell, a corneal endothelial cell, a corneal epithelial cell, a glial retinal cell and a photoreceptor cell.

According to a more preferred embodiment, an animal cell suitable for the invention may be chosen in the group consisting of a smooth muscle cell, in particular a ciliary muscle cell, a retina cell, and a RPE/choroid complex cell.

According to a preferred embodiment, an animal cell suitable for the invention may be a differentiated, non proliferating cell, and more particularly a cell from an adult animal.

According to another preferred embodiment, a biological tissue or organ suitable for the invention may be chosen from a smooth muscle, in particular a ciliary muscle, a retina tissue, a RPE/choroid complex tissue, a corneal endothelium, a corneal epithelium, a glial retinal tissue, or a photoreceptor tissue.

According to one embodiment, as above-explained, the invention may be carried out in vitro, ex vivo, or in vivo.

The animal cells or biological tissues suitable for the invention may be taken from an animal, treated in vitro or ex vivo according to a method of the invention, then return to the animal from which they have been taken or transferred to a distinct histocompatible animal.

According to a preferred embodiment of the invention, any eye cells, in particular retina cells, RPE/choroids complex cells, cells from the ciliary body tissue(s) or from the extra-ocular muscle, may be taken from an animal, grown or not in cell culture, subjected to an ex vivo nucleic acid delivery according to the invention, expanded or not in number, then reimplanted to said animal or to a distinct or to a distinct histocompatible animal.

According to another embodiment, the animal cells or biological tissues may be treated in vivo in accordance with the invention.

As examples of animal that may treated, in vitro, ex vivo or in vivo in accordance with the invention one may mention human, any domestic animals, such as dogs or cats, or any animals of economic values, such as livestock, fishes, poultry, or of labs uses, such as rats, mice or apes.

According to one embodiment, an animal considered in the invention may be a human, and in particular a human suffering from an ocular disease.

Corticosteroids

Corticosteroids are a class of steroid hormones that are produced in the adrenal cortex and are generally grouped into four classes, based on chemical structure As corticosteroids which may be used in accordance with the invention, one may mention any corticosteroids or their derivatives suitable for use in medical, veterinary or experimental practice, and in particular hydrophobic corticoids.

According to a preferred embodiment, a corticosteroid useful for the invention may be in particular a glucocorticoid, and more particularly a synthetic glucocorticoid.

Within the invention, the term "derivative" with respect to the corticosteroid of invention is intended to mean a physiologically or pharmaceutically acceptable salt or ester of said ester, and in particular salts or ester the use of which is authorized in veterinary or medical practice.

As salts of corticosteroids that may be used within the invention, one may mention any pharmaceutically acceptable obtained by acid or base groups addition such as, for acid groups, hydrochloride, hydrobromide, hydroiodide, nitrate, sulfate, bisulfate, phosphate, acid phosphate, sodium phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate or pamoate (i.e., 1,1'-methylene-bis-(2-hydroxy-3-naphthoate)), palmitate, or for base groups, aluminum, calcium, lithium, magnesium, potassium, sodium, zinc, and diethanolamine.

In particular, as salts of corticosteroids useful for the invention, one may mention sodium phosphate of corticosteroids.

As esters of corticosteroids that may be used within the invention, one may mention esters of corticosteroids with carboxylic acid in $C_2$-$C_8$, in particular in $C_3$-$C_6$, such as acetate, propionate, butyrate, pivalate, dipropionate, valerate, caproate, or acetonide.

Among the corticosteroids that may be useful for the invention, one may mention hydrocortisone, cortisone, tixocortol, corticosterone, prednisolone, prednisone, triamcinolone, mometasone, amcinonide, budesonide, desonide, fluocinonide, fluocinolone, halcinonide, betamethasone, dexamethasone, aclometasone, prednicarbate, clobetasone, clobetasol, fluocortolone, fluprednidene, fluometholone, anecortave, derivatives thereof, and mixture thereof.

As examples of corticosteroid derivatives useful for the invention, on may mention hydrocortisone acetate, hydrocortisone-17-butyrate, hydrocortisone-17-valerate, cortisone acetate, tixocortol pivalate, methylprednisolone, triamcinolone acetonide, fluocinolone acetonide, betamethasone sodium phosphate, betamethasone dipropionate, betamethasone valerate, dexamethasone sodium phosphate, aclometasone dipropionate, clobetasone-17-butyrate, clobetasol-17-propionate, fluocortolone caproate, fluocortolone pivalate, fluprednidene acetate, anecortave acetate, and mixture thereof.

According to a particular embodiment, a biological tissue or organ suitable for the invention may be chosen in the group consisting of a smooth muscle, in particular a ciliary muscle, a retina tissue, a RPE/choroid complex tissue, and the corticosteroid is chosen from the group consisting of triamcinolone, anecortave, derivatives thereof, in particular triamcinolone acetonide or anecortave acetate, and mixtures thereof.

According to a particular embodiment, a corticosteroid suitable for the invention may be chosen in the group consisting of corticosterone, prednisolone, triamcinolone, in particular triamcinolone acetonide, fluocinolone, dexamethasone, in particular dexamethasone sodium phosphate, fluometholone, anecortave, in particular anecortave acetate, derivatives thereof, and mixtures thereof.

According to a particular embodiment, a biological tissue or organ suitable for the invention may be a striated muscle and the corticosteroid is chosen from the group consisting of dexamethasone and derivatives thereof, and in particular is dexamethasone sodium phosphate.

According to a preferred embodiment, a corticosteroid suitable for the invention may be chosen from the group consisting of triamcinolone, anecortave, derivatives thereof, in particular triamcinolone acetonide or anecortave acetate, and mixtures thereof.

According to a particular embodiment, an animal cell suitable for the invention may be chosen in the group consisting of a smooth muscle cell, in particular a ciliary muscle cell, a retina cell, a RPE/choroid complex cell, and the corticosteroid may be chosen from the group consisting of triamcinolone, anecortave, derivatives thereof, in particular triamcinolone acetonide, or anecortave acetate, and mixtures thereof.

According to another particular embodiment, an animal cell suitable for the invention may be a striated muscle cell and the corticosteroid may be chosen from the group consisting of dexamethasone and derivatives thereof, in particular dexamethasone sodium phosphate.

Dosage levels of corticosteroid to be used within the invention may be adapted so as to obtain an amount of active ingredient that is effective to obtain the desired intracellular delivery of the nucleic acid.

It should be understood, that the specific dose level will depend upon a variety of factors such as the type of cells, tissue or individual to be treated With respect to an individual, the specific dose level will depend upon a variety of parameters such as the body weight, general health, sex, diet, time, rates of absorption and excretion, combination with other drugs and the severity of the disease being treated.

All those factors and parameters are well-known to an artisan having ordinary skills in the art, and the specific dose level of corticosteroid required may be determined by routine error and trial works.

According to one embodiment, a corticosteroid may be used in vitro or ex vivo according to the invention in an efficient amount ranging from 1 ng/ml to 20 mg/ml, and in particular from 1 µg/ml to 10 mg/ml, and more particularly from 0.5 mg/ml to 5mg/ml.

According to one embodiment, a corticosteroid may be used in vivo according to the invention in an efficient amount ranging from 1 ng/kg to 100 mg/kg, and in particular from 100 µg/kg to 50 mg/kg and more particularly from 0.5 mg/kg to 5 mg/kg.

Nucleic Acids

A nucleic acid to be used in the instant invention may be any nucleic acid of interest, i.e., exhibiting a biological property.

A nucleic acid may be a deoxyribonucleic acid (DNA) molecule, such as a cDNA, gDNA, synthetic DNA, artificial DNA, recombinant DNA, etc., or a ribonucleic acid (RNA) molecule such as mRNA, tRNA, iRNA, siRNA, miRNA, shRNA, catalytic RNA, antisens RNA, viral RNA, and peptidic nucleic acid, and mixtures thereof.

A nucleic acid may be single-stranded or multiple-stranded nucleic acid, and preferably is a double-stranded nucleic acid. A nucleic acid suitable for the invention may comprise hybrid sequences or synthetic or semi-synthetic sequences. It may be obtained by any technique known to persons skilled in the art, and especially by screening libraries, by chemical synthesis, or from biosynthetic origin, or extracted from a virus or from an eukaryotic or a prokaryotic organism or alternatively by mixed methods including chemical or enzymatic modification of sequences obtained by screening libraries.

According to one embodiment, a nucleic acid useful for the invention may comprise any elements suitable for gene expression into an animal cell such as regulatory elements, as for example a promoter region, constitutive, regulated, inducible, or tissue-specific, a transcription termination signal, a secretion sequence, an origin of replication, or a nuclear localization signal sequence.

According to a preferred embodiment, a nucleic acid useful for the invention may comprise any elements suitable for gene expression into an animal eye, and in particular into a human eye, as for example sequences allowing and/or promoting expression in the ciliary body tissue(s) or cells, in the extra-ocular muscle or cells, in the retina cells or in the RPE/choroids complex cells.

Additionally, a nucleic acid useful for the invention may comprise selectable markers useful in selecting, measuring, and monitoring nucleic acid transfer results (transfer to which tissues, duration of expression, etc.). The types of expression systems and reporter genes that may be used or adapted for use in the invention are well known in the art, and may be, as described in the examples section, genes coding for a luciferase activity, an β-galactosidase activity, or a green fluorescent protein activity A nucleic acid according to the invention may contain any nucleotide sequence of any size. The nucleic acid may thus vary in size from a simple oligonucleotide having from 10, 20, 30, 40 or 50 to 100, 200, 300, 400 or 500 bases to a larger molecule having from 600, 700, 800, 900, 1000 to 10 000, 20 000, 30 000, hundred thousand, million or hundred or thousand millions of bases such as a nucleotide sequence including exons and/or introns and/or regulatory elements of any sizes (small or large), a gene of any size, for example of large size, or a chromosome for instance, and may be a plasmid, an episome, a viral genome, a phage, a yeast artificial chromosome, a minichromosome, or an antisense molecule.

In a particularly preferred embodiment, the polynucleotide is a double-stranded, circular DNA, such as a plasmid, encoding a product with biological activity.

A nucleic acid may be prepared and produced according to any conventional recombinant DNA techniques, such as amplification, culture in prokaryotic or eukaryotic host cells, purification, etc. The techniques of recombinant DNA technology are known to those of ordinary skill in the art. General methods for the cloning and expression of recombinant molecules are described in Maniatis et al. (Molecular Cloning, Cold Spring Harbor Laboratories, 1982)

According to one embodiment, a nucleic acid useful for the invention may be any nucleic acid encoding a natural, truncated, artificial, chimeric or recombinant biologically active substance.

A preferred biologically active substance may be any ocular active substance, i.e., a substance capable of exerting a beneficial effect on ocular cells. It may be a substance capable of compensating for a deficiency in or of reducing an excess of an endogenous substance. Alternatively, it may be a substance conferring new properties on the cells. It may be for example an antisense sequence or a polypeptide which can affect the function, morphology, activity and/or metabolism of ocular cells.

Among nucleic acids suitable for the invention are nucleic acids encoding biologically active polypeptides or proteins such as enzymes, blood derivatives, hormones, lymphokines, cytokines, chimiokines, anti-inflammatory factors, growth factors, trophic factors, neurotrophic factors, haematopoietic factors, angiogenic factors, anti-angiogenic factors, inhibitors of metalloproteinase, regulators of apoptosis, coagulation factors, receptors thereof, in particular soluble receptors, a peptide which is an agonist or antagonist of a receptor or of an adhesion protein, antigens, antibodies, fragments or derivatives thereof and other essential constituents of the cell.

Various retina-derived neurotrophic factors have the potential to rescue degenerating photoreceptor cells, and may be delivered trough a method according to the present invention. Preferred biologically active agents may be selected from VEGF, Angiogenin, Angiopoietin-1, DeM, acidic or basic Fibroblast Growth Factors (aFGF and bFGF), FGF-2, Follistatin, Granulocyte Colony-Stimulating factor (G-CSF), Hepatocyte Growth Factor (HGF), Scatter Factor (SF), Leptin, Midkine, Placental Growth Factor (PGF), Platelet-Derived Endothelial Cell Growth Factor (PD-ECGF), Platelet-Derived Growth Factor-BB (PDGF-BB), Pleiotrophin (PTN), Progranulin, Proliferin, Transforming Growth Factor-alpha (TGF-alpha), Transforming Growth Factor-beta (TGF-beta), Tumor Necrosis Factor-alpha (TNF-alpha), Vascular Endothelial Growth Factor (VEGF), Vascular Permeability Factor (VPF), CNTF, BDNF, GDNF, PEDF, NT3, BFGF, angiopoietin, ephrin, EPO, NGF, IGF, GMF, aFGF, NT5, Gax, a growth hormone, [alpha]-1-antitrypsin, calcitonin, leptin, an apolipoprotein, an enzyme for the biosynthesis of vitamins, hormones or neuromediators, chemokines, cytokines such as IL-1, IL-8, IL-10, IL-12, IL-13, a receptor thereof, an antibody blocking anyone of said receptors, TIMP such as TIMP-1, TIMP-2, TIMP-3, TIMP-4, angioarrestin, endostatin such as endostatin XVIII and endostatin XV, ATF, angiostatin, a fusion protein of endostatin and angiostatin, the C-terminal hemopexin domain of matrix metalloproteinase-2, the kringle 5 domain of human plasminogen, a fusion protein of endostatin and the kringle 5 domain of human plasminogen, the placental ribonuclease inhibitor, the plasminogen activator inhibitor, the Platelet Factor-4 (PF4), a prolactin fragment, the Proliferin-Related Protein (PRP), the antiangiogenic antithrombin III, the Cartilage-Derived Inhibitor (CDI), a CD59 complement fragment, vasculostatin, vasostatin (calreticulin fragment), thrombospondin, fibronectin, in particular fibronectin fragment gro-beta, an heparinase, human chorionic gonadotropin (hCG), interferon alpha/beta/gamma, interferon inducible protein (IP-10), the monokine-induced by interferon-gamma (Mig), the interferon-alpha inducible protein 10 (IP10), a fusion protein of Mig and IP10, soluble Fms-Like Tyrosine kinase 1 (FLT-1) receptor, Kinase insert Domain Receptor (KDR), regulators of apoptosis such as Bcl-2, Bad, Bak, Bax, Bik, Bcl-X short isoform and Gax, fragments or derivatives thereof and the like.

According to one embodiment, a nucleic acid useful for the invention may be an antisense nucleic acid for down regulating a gene expression. Antisense nucleic acids of the invention may be nucleic acid fragments capable of specifically hybridizing with a nucleic acid encoding an endogenous ocular active substance or the corresponding messenger RNA. These antisense nucleic acids may be synthetic oligonucleotides, optionally modified to improve their stability and selectivity. They may also be DNA sequences whose expression in the cell produces RNA complementary to all or part of the mRNA encoding, for example, an endogenous ocular active substance. Antisense nucleic acids may be prepared by expression of all or part of a nucleic acid encoding an endogenous ocular active substance, in the opposite orientation. Any length of antisense sequence is suitable for practice of the invention so long as it is capable of down-regulating or blocking expression of the endogenous ocular active substance. Preferably, the antisense sequence may be at least 20 nucleotides in length.

According to an embodiment, an isolated naked nucleic acid suitable for the invention may be chosen from the group consisting of cDNA, gDNA, synthetic DNA, artificial DNA, recombinant DNA, mRNA, tRNA, siRNA, miRNA, shRNA, catalytic RNA, antisens RNA, viral RNA, or peptidic nucleic acid, and mixtures thereof.

Kit

The instant invention also relates to a kit for intracellular delivery of at least one isolated naked nucleic acid in an animal cell, in particular for gene therapy, comprising:

a/ at least one corticosteroid,
b/ at least one isolated naked nucleic acid, and
c/ at least one instruction comprising a first step of treating said animal cell with said corticosteroid for at least 5 minutes to at most 2 hours, and a second step of contacting said treated animal cell with said isolated naked nucleic acid, said second step being carried out immediately after said first step.

Instructions may be in a written, video, or audio form, or may be contained on paper, an electronic medium, or even as a reference to another source, such as a website or reference manual.

Within a kit, the components may be separately packaged or contained.

Other components such as excipients, carriers, other drugs or adjuvants, and administration or injection devices may be supplied in the kit as well.

According to a particular embodiment, an instruction suitable for the invention may further mentions a list of animal cell suitable to be treated with said corticosteroid.

According to a preferred embodiment, cells which may be mentioned may be cell from ophthalmic tissue, and more particularly as previously defined.

According to one embodiment, a kit of the invention may be a kit for preventing or treating an ocular disease.

Use & Compositions

The instant invention also relates to a use of at least one corticosteroid for the preparation of a pharmaceutical composition, as active agent for promoting intracellular delivery of an isolated naked nucleic acid in an individual in need thereof, in particular for gene therapy, said pharmaceutical composition being intended to be administered to said individual at least 5 min to at most 2 hours before administering to said individual said isolated naked nucleic acid.

The instant invention also relates to a corticosteroid in a pharmaceutical composition as active agent for promoting intracellular delivery of an isolated naked nucleic acid in an individual in need thereof, in particular for gene therapy, said pharmaceutical composition being intended to be administered to said individual at least 5 min to at most 2 hours before administering to said individual said isolated naked nucleic acid.

A composition of the invention may be useful for the treatment or prevention of an ocular disease. Within the meaning of the invention, the terms "to prevent", "preventing" or "prevention" are intended to mean the reduction of a risk of occurrence of an event. An event more particularly considered within the invention may be an eye disease.

A composition of the invention may comprise any pharmaceutically compatible or physiologically acceptable carrier, excipient or diluent, preferably sterile, and in particular selected from neutral to slightly acidic, isotonic, buffered saline, aqueous or oleaginous solutions or suspensions and more preferably from sucrose, trehalose, surfactants, proteins and amino acids.

A pharmaceutically compatible or physiologically acceptable carrier, excipient or diluent may be formulated using suitable dispersing, wetting, suspending, soothing, isotonic or viscosity building agents, stabilizers, preservatives and appropriate buffer to form an isotonic solution.

A nucleic acid suitable for the invention may be prepared in any forms of compositions known in the art, provided that the nucleic acid is in naked form.

According to a preferred embodiment, a composition in accordance with the invention may be intended for ocular administration.

According to one embodiment, a composition with a viscosity greater than that of simple aqueous solutions may be desirable, for example for increasing ocular absorption, for decreasing variability in dispensing the formulations, for decreasing physical separation of components of a suspension or an emulsion and/or otherwise for improving the ophthalmic formulation. Viscosity building agents useful for the invention may include, for example, polyvinyl alcohol, polyvinyl pyrrolidone, methyl cellulose, hydroxypropyl methylcellulose, hydroxyethyl cellulose, carboxymethyl cellulose, hydroxypropyl cellulose or other agents known to those skilled in the art. Such agents are typically employed at a level of from about 0.01 to about 2 wt. %.

According to one embodiment, a composition or a method in accordance with the invention may be intended for preventing and/or treating ocular diseases and disorders.

As examples of ocular diseases and disorders which may be considered in the invention, one may mention ocular proliferative diseases, ocular neurodegenerative diseases, such as inhibited retinal dystrophies of any type, ocular infectious diseases, ocular or intraocular inflammatory diseases, such as conjunctivitis, keratitis, endothelitis, uveitis, choroiditis, retinitis, retinochoro[iota]ditis, anterior and intermediate uveitis, and inflammatory optic neuropathies, retinal degenerations, in particular inherited retinal dystrophies or retinitis pigmentosa, peripheral retinal degeneration, macular degeneration such as dry age-related macular degeneration, ischemic and neovascular proliferative diseases such as retinopathy, in particular retinopathy of prematurity and diabetic retinopathy, retinal vascular diseases, ocular ischemia syndrome and other vascular anomalies, macular oedema associated with age related macular degeneration, diabetic retinopathy, intraocular inflammation or retinal dystrophies, choroidal disorders and tumors, vitreous disorders, glial proliferation such as proliferative vitreo retinopathy and glial proliferation associated to diabetic pre-retinal angiogenesis, angiogenesis, glaucoma, open angle glaucoma, neovascular glaucoma, macular pucker also called epiretinal membrane, retinal wrinkling, premacular fibrosis, and cellophane maculopathy, etc

FIGURES

FIG. 1: Illustrates the devices used, respectively, for intravitreous (IVT) injection of plasmid and the chemical agents assayed (FIG. 1A) or for intravitreous electrotransfer (ET) of the plasmids (FIGS. 1B and 1C).

IVT injection was performed using a 30 G needle on a 300 µl microfine syringe (ref. 320837, 0.3 mL, U-100, BD).

Intravitreous ET was performed using iridium/platinum (10/90) electrodes. The cathode was shell-like casted so as to fit the eyeball, and positioned under the eye. The anode was in the form of a half-rim and place into contact with the upper part of the eye. An electrotransfer generator was set to deliver eight consecutive pulses (180 ms between pulses) of 80 V each and 20 ms duration (5 Hz).

Figure 2:
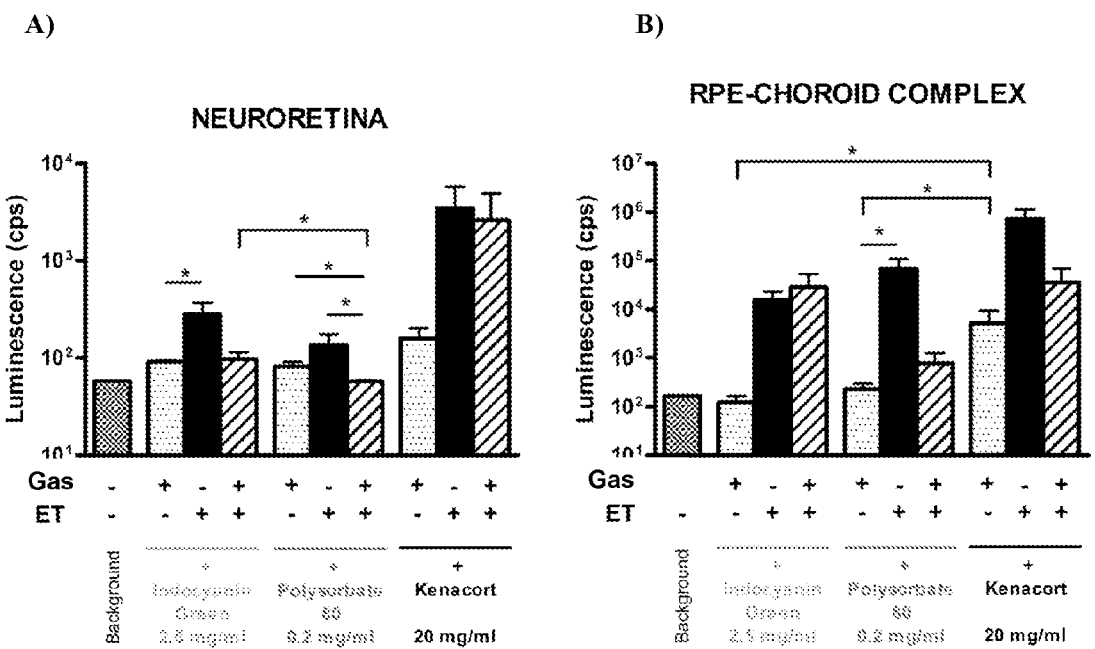

FIG. 2: Illustrates the intracellular delivery of naked plasmids and gene expression in the neuroretina (FIG. 2A) and the RPE-choroid complex (FIG. 2B) of IVT pre-injection of 10 µl of the corticosteroid pharmaceutical specialty KENACORT® at 20 mg/ml (triamcinolone acetonide (TA) as active agent and polysorbate 80 as excipient), Indocyanine Green at 2.5 mg/ml or Polysorbate 80 at 0.2 mg/ml 30 min before IVT injection of the plasmid pVAX2-Luc (30 µg in 10 µl in NaCl 0.45%), followed by gas injection or ET application [8×(80V; 20 ms ; 5 Hz)] or combination of both immediately upon IVT injection of the plasmid. Luminescence is expressed in counts/s (cps). The results are expressed as the mean±sem of 4 independent experiments.

Figure 3:
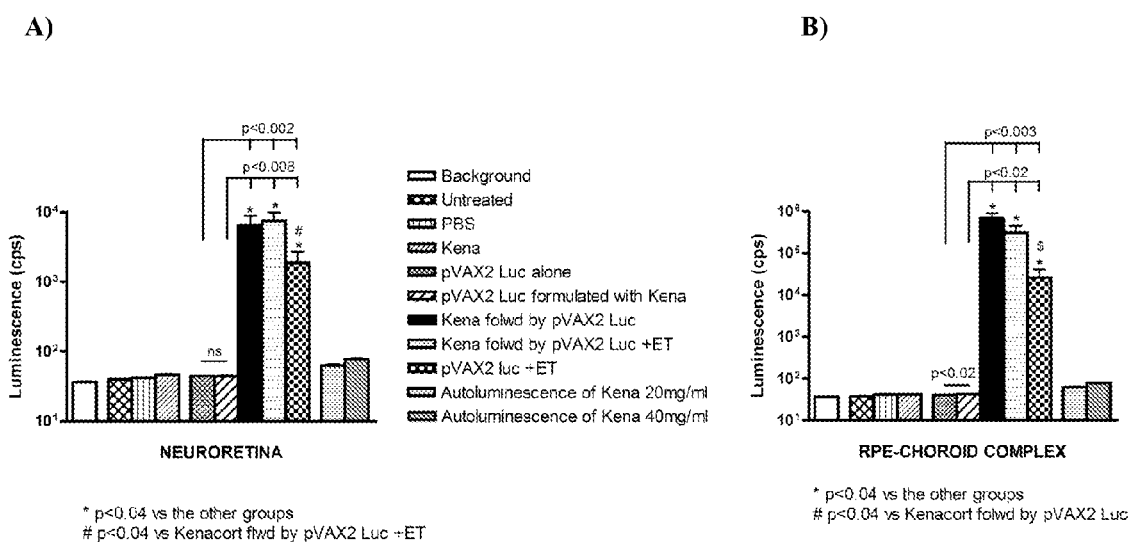

FIG. 3: Illustrates the intracellular delivery of naked plasmids and gene expression in the neuroretina (FIG. 3A) and the RPE-choroid complex (FIG. 3B) of IVT injection of the naked plasmid pVAX2-Luc (10 µg in 10 µl in NaCl 0.45%) alone, or simultaneously with 10 µl of KENACORT® at 20 mg/ml, or preceded by IVT pre-injection of KENACORT® 30 min before IVT injection of the plasmid alone, or followed by ET application [8×(80V; 20 ms; 5 Hz)] immediately upon IVT injection of the plasmid alone, or preceded by IVT pre-injection of KENACORT® and followed by ET application. Luminescence is expressed in counts/s (cps). The results are expressed as the mean±sem of 6 independent experiments.

Figure 4:
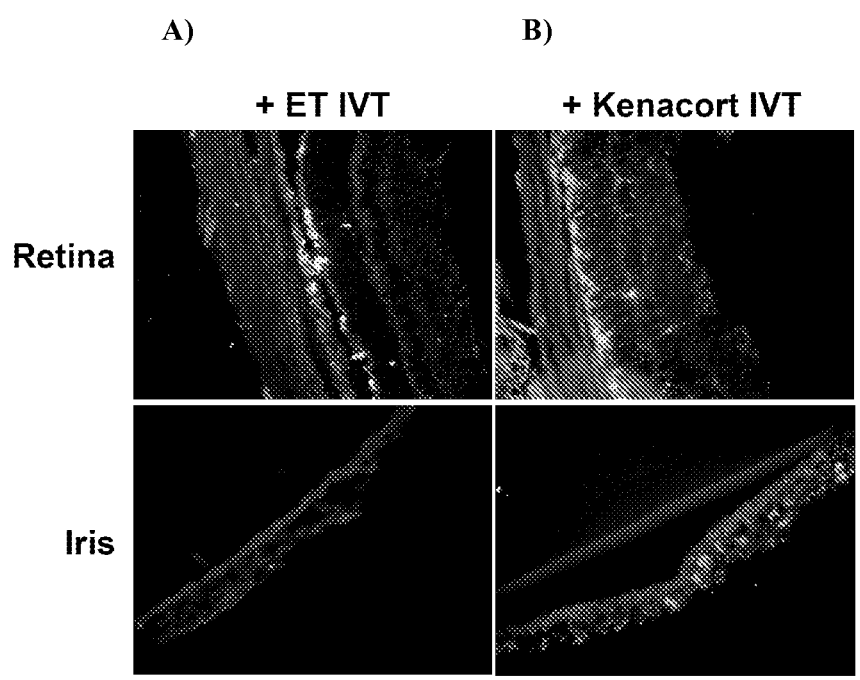

FIG. 4: Illustrates the intracellular delivery of naked plasmids and gene expression in the retina and the iris of IVT injection of the naked plasmid pEGFPC1 (10 µg in 10 µl in NaCl 0.45%) preceded by IVT pre-injection with 10 µl of KENACORT® at 20 mg/ml 30 min before IVT injection of the plasmid alone, or followed by ET application [8×(80V; 20 ms; 5 Hz)] immediately upon IVT injection of the plasmid alone. The pictures were acquired with a fluorescence microscope (Leica, Switzerland) and numeric microphotographs were taken with a constant exposure time for all sections 7 days after the transfection. Images are representative of an experiment repeated twice.

Figure 5:
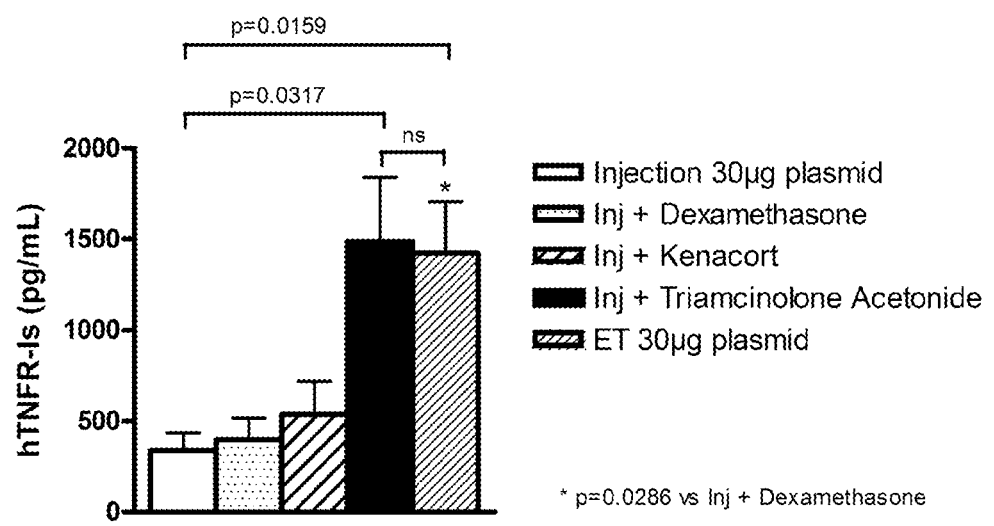

FIG. 5: Illustrates the intracellular delivery of naked plasmids and gene expression in a smooth muscle, the ciliary muscle, of intramuscular pre-injection of dexamethasone (DEX), triamcinolone acetonide (TA) or KENACORT® at 20 mg/ml (10 µl), 60 min before intramuscular injection of the naked plasmid pVAX2-hTNFR/mIgG1 (30 µg in 10 µl in NaCl 0.45%). ET applied immediately upon intramuscular injection of the plasmid not preceded with a corticosteroid pre-injection is performed as control. Luminescence is expressed in counts/s (cps). The results are expressed as the mean±sem of 4 independent experiments.

Figure 6:
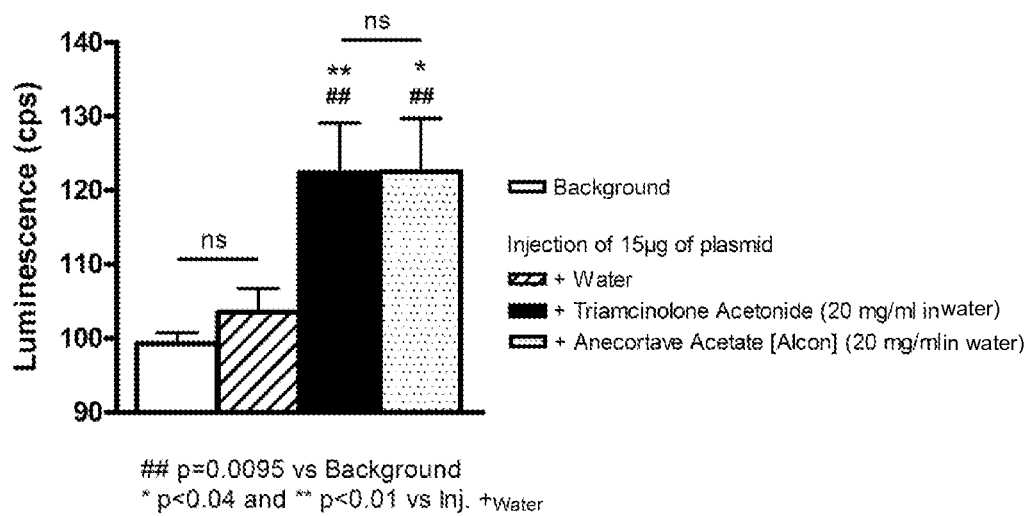

FIG. 6: Illustrates the intracellular delivery of naked plasmids to a smooth muscle, the ciliary muscle, and subsequent gene expression in ocular media. Intramuscular pre-injection of triamcinolone acetonide (TA) or anecortave acetate (AA) at 20 mg/ml (10 µl) was carried out 45 min before intramuscular injection of the naked plasmid pGLuc (15 µg in 10 µl in NaCl 0.45%). No transfection or water instead of corticosteroid was used as control. Luminescence is expressed in counts/s (cps). The results are expressed as the mean±sem of 4 to 6 independent experiments.

Figure 7:
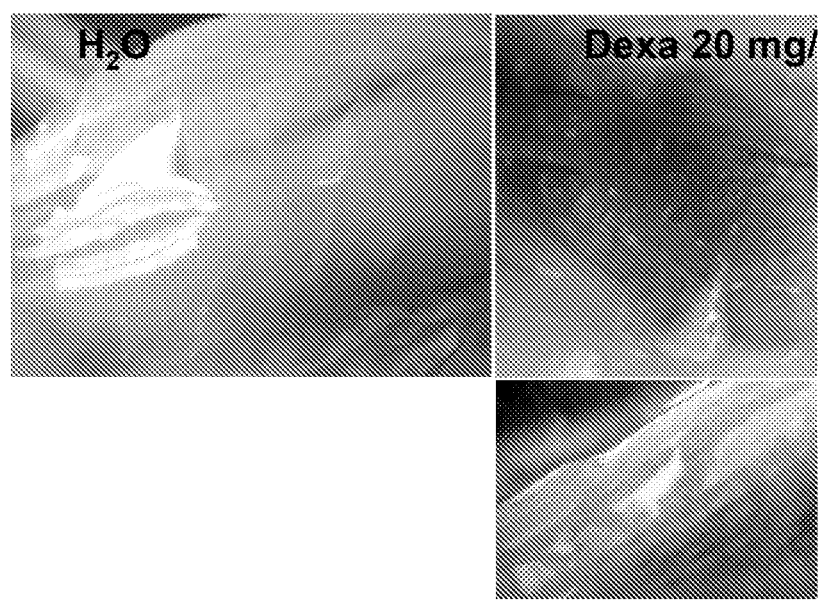

FIG. 7: Illustrates the intracellular delivery of naked plasmids and gene expression in a striated muscle, the tibialis anterior muscle of rats, of intramuscular pre-injection of dexamethasone (DEX) or triamcinolone acetonide (TA) at 20 mg/ml (100 µl) 15-30 min before intramuscular injection of the naked plasmid pVAX1-LacZ (100 µg in 100 µl in NaCl 0.45%). Water instead of corticosteroid was used as control. The cells expressing the β-galactosidase were stained with the colorimetric agent X-gal. The pictures were acquired with a numerized camera (Coolpix; Nikon, Fnac, Paris, France) 5 days after the transfection. Images are representative of an experiment repeated twice.

Figure 8:
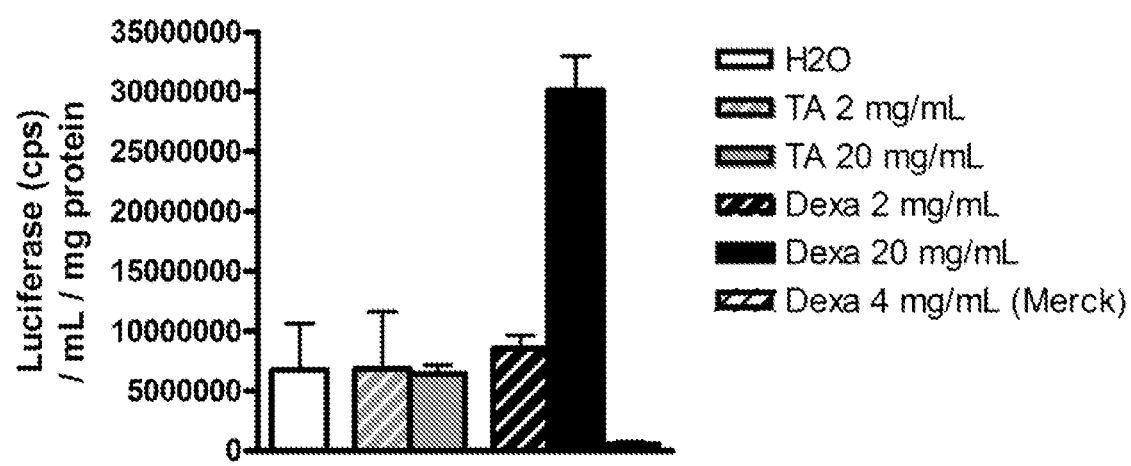

FIG. 8: Illustrates the intracellular delivery of naked plasmids and gene expression in a striated muscle, the tibialis anterior muscle of mouse, of intramuscular pre-injection of dexamethasone (DEX) or triamcinolone acetonide (TA) at 2 or 20 mg/ml (30 µl) 30-45 min before intramuscular injection of the naked plasmid pVAX2-Luc (30 µg in 30 µl in NaCl 0.45%). Luminescence is expressed in counts/s/ml/mg of protein (cps/ml/mg). The results are expressed as the mean±sem of 3 independent experiments.

In the present invention, "one" is intended to mean "at least one", except otherwise stated.

In the present invention, the ranges of values mentioned with the expressions "between . . . and . . . " and "from . . . to . . . " include the lower and the upper limits.

Other aspects and advantages of the present invention will be described in the following examples, which should be regarded as illustrative and not limiting the scope of the present application.

EXAMPLES

In the present invention, inventors have designed a novel intracellular delivery method to specifically transfer naked isolated nucleic acids into non-competent or poorly competent cells or tissues without the need of additional chemical or biological vectors or physical techniques. Plasmid encoding for green fluorescent protein (GFP), luciferase (Luc), β-galactosidase or hTNFR-Is/mIgG1 chimer protein have been used to trace and dose post-transfection gene expression.

Materials and Methods

Animals

Female Lewis rats, 6-7 weeks old weighing 150-200 g (Elevage Janvier, Le Genest Saint Isle, France) or strain C56BL6J p50 null mice 1 year old were used. Experiments were conducted in accordance with the ARVO Statement for the Use of Animals in Ophthalmic and Vision Research.

Rats and mice were held for 1 week before inclusion in the study. For experiments, rats were anesthetized with intramuscular injection of Ketamine (75 mg/kg) (Virbac, France) and Largactil (0.5 mg/kg) (Sanofi-Aventis, France), except for transfection experiments conducted intramuscularly where the Ketamine and Largactil injections were carried out intraperitoneally. The mice were anesthetized with intraperitoneal pentobarbital injection (40 mg/kg). At the end of the experiments, rats and mice were sacrificed by an overdose of pentobarbital.

According to the organ assayed, the eyes were enucleated or the skeletal muscles were removed.

Chemical Agents

The corticosteroids (CCs) used in the experiments were the pharmaceutical specialty KENACORT®, the dexamethasone (DEX), the triamcinolone acetonide (TA) and the synthetic corticoid anecortave acetate (AA). Those corticoids were obtained from Sigma-Aldrich, Saint-Quentin Fallavier, France; DEX and TA) and Alcon (fort Worth, texas, USA).

The corticosteroids were diluted in water and used at concentrations of 2 or 20 mg/ml. For IVT injection and injection in the ciliary muscle a volume of 10 µl was used; for injection in the skeletal muscle volumes of 30 µl and 100 µl were used respectively in the mouse and rat.

The colorant indocyanine green was obtained from and was used at 2.5 mg/ml in water.

The polysorbate 80 (excipient in the pharmaceutical specialty KENACORT® (ROCHE) was obtained from and was used at 0.2 mg/ml in water.

The isovolumetric fluorinated gases used in the experiments were C2F6 and SF6.

Plasmids pVAX2 consists in a pVAX1 plasmid (Invitrogen) in which the promoter was replaced by the pCMVβ plasmid promoter. The pCMVβ (Clontech) was digested with EcoRI, then blunt ended by the Klenow fragment, and finally digested by BamHI. A resulting 629 bp fragment corresponding to the CMV promoter was purified after agarose gel electrophoresis. This promoter was ligated into a HindI-BamHI pVAX1 fragment to give pVAX2.

pVAX2-Luc is a 4.6 kb plasmid vector encoding a cytosolic firefly luciferase plus protein under the control of the CMV β-promoter.

Plasmid pVAX2 hTNFR-Is/mIgG1 is a 4.3 kb plasmid encoding a chimeric protein of human TNF-α soluble receptor type I (hTNFR-Is) linked to the Fc portion of immunoglobulin G1 (IgG1) cloned into a pVAX2 backbone. This chimeric protein has a longer half-life compared to the natural monomeric equivalent hTNFR-Is.

Plasmid pEGFP-C1 is a 4.7 kb plasmid carrying the cytosolic Green Fluorescent Protein gene under control of a CMV promoter (Clontech, Palo Alto, Calif.).

pVAX1-LacZ is a 6.1 kb plasmid containing the LacZ gene reporter gene under the control of a CMV promoter (Invitrogen, Carlsbad, Calif., USA).

pGLuc is a 5.8 kb plasmid vector encoding a secreted Gaussia luciferase protein under the control of a CMV promoter (Lux Biotechnology).

Plasmids were grown in Escherichia coli and purified on column (Endofree plasmid Giga Kit, Qiagen, Courtaboeuf, France). Endotoxin-free plasmids were diluted in NaCl 0.45% at the expected concentration.

Injections

Intravitreous (IVT) injection in the vitreous humor of the eye (FIG. 1A) or intramuscular injection into the temporal superior quadrant of the ciliary muscle was performed using a 30 G needle on a 300 µl microfine syringe (BD Biosiences, Le Pont de Claix, France). To reach the ciliary muscle located below the sclera posterior to the limbus, the intra ciliary muscle injection was carried out through a tunneled corneal incision. When the needle had crossed the limbus, it was inserted slightly deeper for a distance of 1 mm and the solutions were injected.

Intramuscular injection in the rat tibialis anterior muscle or forelimb muscle was performed using a 25 G needle on a 1 ml syringe (Terumo, Dominique Dutscher, Brumath, France). Intramuscular injection in the mouse tibialis anterior muscle was carried out with a 30 G needle on a 300 µl microfine syringe (BD Biosiences).

Electrotransfer (ET)

The protocol used for the ciliary muscle electrotransfer is described in details in WO 2006/123243 which is herein incorporated by reference.

Briefly, for electrotransfer experiments of the ciliary muscle, the eye was exposed and held in position using a surgical sheet. An iridium/platinum electrode (500 µm in diameter), naked on 2 mm and with silicone on the rest of its length, was inserted through the corneal tunnel and the cathode. The anode return electrode consisted of an iridium/platinum 0.3 mm thick sheet, 5 mm length and 2.5 mm wide, designed to exactly fit the rat scleral surface overlying the ciliary body.

For intravitreous electrotransfer experiments, the eyes were surgically prepared as above-exposed for ciliary muscle ET. The intravitreous ET was performed using iridium/platine electrodes. The cathode was shell-like casted so as to fit the eyeball, and positioned under the eye. The anode was in the form of a half-rim and place into contact with the upper part of the eye.

Electrotransfer generator was set to deliver eight consecutive pulses (180 ms between pulses) of 15 Volts (ciliary muscle) or 80 Volts (intravitreous) and 20 ms duration each were delivered using the above system. This electric field intensity did not cause any clinically detectable structure damage or tissue burns.

GFP Histochemistry

At day 8 after transfection of pEGFP-C1, the eyes were enucleated, fixed in 4% paraformaldehyde for 1 hour, rinsed in 1× PBS, embedded in OCT (Optimal Cutting Temperature) compound and cryo-sectioned (8 µm). Sagital 10 µm sections were performed (parallel to the optic axis). Sections were examined under a fluorescence microscope (Leica, Switzerland) and numeric microphotographs were taken with a constant exposure time for all sections.

In Vitro Measurement of Luciferase Activity

Rats receiving intravitreal injection of pVAX2-luc were sacrificed on day 7 after treatment. The eyes were enucleated and dissected under an operating microscope, the neuroretina and RPE/choroid complex removed, snap frozen in liquid nitrogen and kept at −80° C. until tested.

Rats receiving injection of pGLuc in the ciliary muscle were sacrificed on day 7 after treatment. Intraocular fluids were collected on enucleated eyes, clarified by centrifugation and the supernatants stored at −20° C. until tested.

Mouse receiving injection of pVAX2-luc in the tibialis anterior muscle were sacrificed on day 7 after treatment. The tibialis anterior muscle was removed, snap frozen in liquid nitrogen and kept at −80° C. until tested.

Tissue samples were then homogenized in 0.3 ml (rat neuroretina and RPE/choroid complex) or 1.0 ml (mouse tibialis anterior muscle) of cell culture lysis reagent (Promega, Charbonniere, France) supplemented with protease inhibitor cocktail (Boehringer, Mannheim, Germany) (one tablet for 50 ml). After centrifugation 10 min at 15 000 g and 4° C., tissue lysate supernatant was collected.

The luciferase activity was assessed on 10 µl of sample (tissue lysate supernatant or ocular fluid) placed in a white 96 wells plate.

The detector was a Wallac Victor luminometer (EG&G Wallac, Evry, France) which adds 50 µl of luciferase assay substrate or Gaussia luciferase assay substrate (Promega) to the sample (tissue lysate supernatant or ocular fluid respectively) and integrates the light produced by the sample during 10 s. Results are given for the whole sample in counts per second (cps) or in cps/ml/mg of protein.

Effect of hTNFR-Is/m1gG1 Plasmid Electro-transfer

The production of hTNFR-Is in the ocular media was evaluated on the 7th day after pVAX2 hTNFR-Is/mlgG1 injection to the ciliary muscle. The ocular media from right and left eyes were obtained and evaluated separately for each eye. Ocular media from the contra lateral, not treated eyes were used as control of hTNFR-Is levels.

Levels of hTNFR-Is receptors were measured by ELISA using a human receptor type I specific kit (Duoset, R&D Systems, Abingdon, UK), according to the manufacturer's instructions.

β-galactosidase in the Tibialis Anterior Muscle

Rats receiving injection of pVAX1-LacZ in the tibialis anterior skeletal muscle were sacrificed on day 5 after treatment. The skeletal muscles were removed, fixed for 1 h at 4° C. in 2% paraformaldehyde and 0.2% glutaraldehyde in phosphate-buffered saline (PBS). They were rinsed three times in PBS before being incubated overnight at room temperature with 1 mg/ml_1 X-gal (5-bromo-4-chloro-3-indolyl galactopyranoside; Sigma-Aldrich, Saint-Quentin-Fallavier, France) in PBS containing 5 mM of K3Fe(CN)6, 5 mM of K4Fe(CN)6, 2 mM of MgCl2 and 0.02% NP-40. After washing with PBS, direct imaging from the outside of the muscle was carried out using a numerized camera (Coolpix; Nikon, Fnac, Paris, France).

Statistical Analysis

Results are expressed as means+/−standard error of the mean (SEM). Data were compared using the nonparametric Mann-Whitney U-test. P<0.05 was considered statistically significant.

Example 1

KENACORT® Improves Delivery of a Naked Plasmid and Gene Expression into the Retina after Intravitreous (IVT) Injection Cells of the neuroretina and of the RPE-choroid complex, and in general ophthalmic cells, are very difficult to transfect, and are known to be non-competent in regard to naked nucleic acids (in contrast with others cells such striated muscle cells). Those cells are known to require auxiliary transfection techniques such chemical or biological vector or electrotransfer to allow nucleic acids transfection.

The effect of various chemical agents on the RPE-choroid complex gases injection or electrotransfer-induced intracellular delivery of the naked plasmid pVAX2-Luc and gene expression of the luciferase in neuroretina was evaluated.

Thirty µg of naked pVAX2-Luc in 10 µl in NaCl 0.45% was injected intravitreously in one eye of anaesthetized rats (the contra lateral eye was used as control) immediately followed by gas injection (C2F6 or SF6) or ET application [8×(80V; 20 ms; 5 Hz)] or combination of both.

In some experiments, 30 minutes before administration of the plasmid, the eyes were pretreated by IVT injection of 10 µl of Indocyanin Green (2.5 mg/ml), Polysorbate 80 (0.2 mg/ml) or KENACORT® (20 mg/ml).

7 days after the treatment the animals were sacrificed, the eyes were enucleated and dissected under an optical microscope to isolate the neuroretina and the RPE-choroid complex and the luminescence of the luciferase was measured.

In the neuroretina, KENACORT® induced a slight increase in efficiency of cells transfection induced with gases injection and a dramatic improvement in efficiency of transfection induced with ET or with gases injection and ET (FIG. 2A). By contrast, Indocyanin Green or Polysorbate 80 proved to be less efficient (FIG. 2A).

In the RPE-choroid complex, KENACORT® induced a noticeable increase in efficiency of cells transfection induced with gases injection or with ET or with gases injection and ET (FIG. 2B). By contrast, Polysorbate 80 and Indocyamin Green proved to be less efficient to improve the efficacy of gases injection whereas they improved, in a certain extent, the efficiency of ET (FIG. 2B).

Example 2

Pre-treatment with Corticosteroid is Able to Induce Intracellular Delivery of Naked Plasmid and Gene Expression Ten µg of naked pVAX2-Luc in 10 µl in NaCl 0.45% was injected intravitreously in one eye of anaesthetized rats (the contra lateral eye was used as control).

The plasmid injection was either carried out a) alone, b) in combination with 10 µl KENACORT® (20 mg/ml), c) preceded 30 min before by IVT injection of KENACORT®, d) immediately followed by ET application [8×(80V; 20 ms; 5 Hz)], or e) preceded 30 min before by IVT injection of KENACORT® and immediately followed by ET.

As controls were taken untreated eyes, eyes treated with PBS or treated with KENACORT® alone.

7 days after the treatment the animals were sacrificed, the eyes were enucleated and dissected under an optical microscope to isolate the neuroretina and the RPE-choroid complex and the luminescence of the luciferase was measured.

As illustrated by FIGS. 3A and 3B, IVT injection of pVAX2-Luc preceded 30 minutes before by injection with KENACORT® induced a dramatic expression of luciferase in neuroretina as well as in the RPE-choroid complex. The level of expression obtained with KENACORT® was equivalent to the level of expression obtained by ET in neuroretina but far superior to ET in the RPE-choroid complex.

The combination of both methods, corticosteroid pre-treatment and ET, did not amount to a superior level of expression.

In contrast, IVT injection of the naked plasmid alone or simultaneously with KENACORT® did not induce expression of luciferase.

Those results suggest that a short pre-treatment of ophthalmic cells with corticosteroid allows naked isolated nucleic acids to be efficiently transfected and expressed into naturally non competent cells.

Example 3

Localization of EGFP Expression in Retina and Iris Following Transfection of pEGFPC1 After Pre-treatment with Corticosteroid or Followed by ET Ten µg of naked pEGFPC1 in 10 µl in NaCl 0.45% was injected intravitreously in one eye of anaesthetized rats (the contra lateral eye was used as control).

The plasmid injection was either a) preceded 30 min before by IVT injection of 10 µl of KENACORT® (20 mg/ml) or b) immediately followed by ET application [8×(80V; 20 ms; 5 Hz)].

At day 8 after transfection, the eyes were enucleated, fixed in 4% paraformaldehyde for 1 hour, rinsed in 1×PBS, embedded in OCT compound and cryo-sectioned (10 µm). Sections were examined under a fluorescence microscope (Leica, Switzerland) and numeric microphotographs were taken with a constant exposure time for all sections.

As illustrated by FIG. 4, IVT pre-injection KENACORT® 30 min before injection of naked pEGFPC1 induced an improved and localized expression of EGFP in the retina and the iris compared to transfection with ET.

Example 4

Improvement of Intracellular Delivery and Expression of hTNFR-Is/mIgG1 Chimer Protein in the Aqueous Humor Upon Transfection of the Ciliary Muscle Subjected to Intramuscular Pre-injection with Corticosteroids Ciliary smooth muscle cells are also cells of the ophthalmic tissue known to be non-competent cells in regard to naked plasmid. Those cells are known to require auxiliary transfection techniques such chemical or biological vector or electrotransfer to allow nucleic acid transfection.

Thirty µg of naked pVAX2-hTNFR-Is/mIgG1 in 10 µl in NaCl 0.45% was injected in the ciliary muscle of one eye of anaesthetized rats (the contra lateral eye was used as control).

The plasmid injection was either preceded 60 min before by intramuscular injection of 10 µl of KENACORT® (20 mg/ml), or of dexamethasone (DEX, 20 mg/ml), or of triamcinolone acetonide (TA, 20 mg/ml), or immediately followed by ET application [8×(15V; 20 ms; 5 Hz)].

Plasmid alone and ET applied immediately upon intramuscular injection of the plasmid not preceded with a corticosteroid pre-injection were taken as controls.

As illustrated by FIG. 5, TA was able to dramatically improve the level of expression of hTNFR-Is in the aqueous humor of eye when compared with injection of the naked plasmid alone. The obtained level of expression was comparable to that obtained with ET.

Example 5

Improvement of Intracellular Delivery and Expression of Luciferase in the Aqueous Humor Upon Transfection of the Ciliary Muscle Subjected to Intramuscular Pre-injection with TA or AA Fifteen µg of naked pGLuc in 10 µl in NaCl 0.45% was injected in the ciliary muscle of one eye of anaesthetized rats (the contra lateral eye was used as control).

The plasmid injection was preceded 45 min before by intramuscular injection of 10 µl of triamcinolone acetonide (TA, 20 mg/ml) or anecortave acetate (AA, 20 mg/ml), a synthetic corticosteroid.

No injection and pre-injection with water were performed as controls.

As illustrated by FIG. 6 and by Table I below, TA and AA were able to dramatically improve the level of expression of Luciferase in the aqueous humor of eye when compared to injection of the naked plasmid alone.

TABLE I

Level of expression of Luciferase in aqueous humor upon transfection of the ciliary muscle

| Assays | Pre-treatment | | | |
| --- | --- | --- | --- | --- |
| | None (background) | Water | TA 20 mg/ml | AA 20 mg/ml |
| Number of experiments | 4 | 4 | 6 | 6 |
| Luciferase (cps) Mean ± sem | 99.3 ± 1.5 | 103.5 ± 3.2 | 122.3 ± 6.8 | 122.5 ± 7.2 |

Example 6

Intracellular Delivery and Expression of Luciferase in the Tibialis Anterior Muscle (Striated Muscle) of Rats or Mice Subjected to Intramuscular Pre-injection with TA or AA One hundred µg of pVAX1-LacZ or thirty µg of naked pVAX2-Luc in 100 or 30 µl in NaCl 0.45% were, respectively, injected into the tibialis anterior muscle of rats or into the tibialis anterior muscle of mice.

In the rats, the plasmid injection was preceded 15-30 min before by intramuscular injection of 100 µl of triamcinolone acetonide (TA) or dexamethasone (DEX) at 2 or 20 mg/ml.

In the mice, the plasmid injection was preceded 30 min before by intramuscular injection of 30 μl of triamcinolone acetonide (TA) or dexamethasone (DEX) at 2 or 20 mg/ml, or soluble DEX at 4 mg/ml.

Pre-injection with water was performed as control.

As illustrated by FIGS. 7 and 8 and by Table II below, pre-treatment with DEX dramatically improved gene expression of β-galactosidase and Luciferase in those muscles.

TABLE II

Level of expression of Luciferase in tibialis anterior muscle upon transfection with naked plasmid with or without pre-treatment with corticosteroid

| | | Pre-treatment | | | | |
|---|---|---|---|---|---|---|
| Assays | Water | TA 2 mg/ml | TA 20 mg/ml | DEX 2 mg/ml | DEX 20 mg/ml | DEX soluble 4 mg/ml |
| Number of experiments | 3 | 3 | 3 | 3 | 3 | 3 |
| | | | Luciferase (cps) | | | |
| means ($10^6$) | 6.749 | 6.849 | 6.431 | 8.526 | 30.13 | 0.5356 |
| sem ($10^6$) | 3.892 | 4.772 | 0.7405 | 1.136 | 2.841 | 0.2369 |

The invention claimed is:

1. A method for intracellular delivery of at least one isolated naked nucleic acid into an ophthalmic tissue comprising a non-competent cell, said method comprising at least the steps of:
    a/ contacting said ophthalmic tissue with an efficient amount of at least one active corticosteroid for a period of time ranging from at least five minutes to at most two hours; and, immediately following step a/,
    b/ contacting said ophthalmic tissue treated in step a/ with an efficient amount of at least one isolated naked nucleic acid by injection into ciliary muscle;
    wherein:
        said at least one active corticosteroid is selected from the group consisting of triamcinolone, anecortave, derivatives thereof, and mixture thereof, and
        said method does not include an electrotransfer step.

2. The method according to claim 1, wherein said period of time of step a/ ranges from 10 to 90 minutes.

3. The method according to claim 1, wherein said ophthalmic tissue is selected from the group consisting of ciliary muscle, retina tissue, Retinal Pigment Epithelium/choroid complex tissue, corneal endothelium, corneal epithelium, and glial retinal tissue.

4. The method according to claim 1, wherein said isolated naked nucleic acid is selected from the group consisting of cDNA, gDNA, synthetic DNA, artificial DNA, recombinant DNA, mRNA, tRNA, siRNA, miRNA, shRNA, catalytic RNA, antisense RNA, viral RNA, peptidic nucleic acid, and mixtures thereof.

5. As method for promoting intracellular delivery of an isolated naked nucleic acid in an individual in need thereof, the method comprising:
    administering to said individual a pharmaceutical composition comprising at least one corticosteroid as an active agent at least 5 minutes to at most 2 hours before administering to said individual said isolated naked nucleic acid, said isolated naked nucleic acid being administered by injection in a ciliary muscle in an ophthalmic tissue comprising a non-competent cell,
    wherein;
        said method does not include an electrotransfer step, and
        said at least one active corticosteroid is selected from the group consisting of triamcinolone, anecortave, derivatives thereof, and mixture thereof.

6. A method for preventing and/or treating a disease selected from ocular proliferative diseases, ocular neurodegenerative diseases, ocular infectious diseases, ocular or intraocular inflammatory diseases, retinal degenerations, peripheral retinal degeneration, macular degeneration, ischemic and neovascular proliferative diseases, retinal vascular diseases, ocular ischemia syndrome and other vascular anomalies, macular oedema associated with age related macular degeneration, diabetic retinopathy, intraocular inflammation or retinal dystrophies, choroidal disorders and tumors, vitreous disorders, glial proliferation, angiogenesis, glaucoma, open angle glaucoma, neovascular glaucoma, macular pucker also called epiretinal membrane, retinal wrinkling, premacular fibrosis, and cellophane maculopathy, comprising the method of claim 5.

* * * * *